United States Patent
von Felde

(10) Patent No.: US 9,139,851 B2
(45) Date of Patent: Sep. 22, 2015

(54) USE OF AN ENSILING AGENT FOR THE TREATMENT OF UNCHOPPED BEETS

(75) Inventor: Andreas von Felde, Soltau, DE (US)

(73) Assignee: KWS SAAT SE, Einbeck (DE)

( * ) Notice: Subject to any disclaimer, the term of this patent is extended or adjusted under 35 U.S.C. 154(b) by 364 days.

(21) Appl. No.: 13/520,584

(22) PCT Filed: Feb. 17, 2011

(86) PCT No.: PCT/DE2011/000142
§ 371 (c)(1),
(2), (4) Date: Jul. 5, 2012

(87) PCT Pub. No.: WO2011/100956
PCT Pub. Date: Aug. 25, 2011

(65) Prior Publication Data
US 2012/0322120 A1    Dec. 20, 2012

(30) Foreign Application Priority Data
Feb. 18, 2010    (DE) .......................... 10 2010 008 516

(51) Int. Cl.
| | |
|---|---|
| *A23B 7/154* | (2006.01) |
| *C12P 7/06* | (2006.01) |
| *A23L 3/3517* | (2006.01) |
| *A23L 3/3508* | (2006.01) |
| *A23K 3/03* | (2006.01) |
| *C12P 19/12* | (2006.01) |
| *C13B 99/00* | (2011.01) |

(52) U.S. Cl.
CPC ................ *C12P 7/065* (2013.01); *A23B 7/154* (2013.01); *A23K 3/03* (2013.01); *A23L 3/3508* (2013.01); *A23L 3/3517* (2013.01); *C12P 19/12* (2013.01); *C13B 99/00* (2013.01); *Y02E 50/17* (2013.01)

(58) Field of Classification Search
CPC .... A23B 7/154; A23L 3/3508; A23L 3/3517; C13B 99/00; A23K 3/03; C12P 7/065; Y02E 50/10
USPC ............................................ 426/323; 127/43
See application file for complete search history.

(56) References Cited

U.S. PATENT DOCUMENTS

| | | | | |
|---|---|---|---|---|
| 3,062,659 | A  * | 11/1962 | Hyson et al. ................... | 426/312 |
| 6,183,794 | B1 * | 2/2001  | Kaesler et al. ................. | 426/335 |
| 6,867,233 | B2 * | 3/2005  | Roselle et al. ................. | 514/557 |

FOREIGN PATENT DOCUMENTS

| | | |
|---|---|---|
| DE | 59467 A | 12/1967 |
| DE | 2404462 A1 | 8/1974 |
| DE | 226764 A1 | 9/1985 |

OTHER PUBLICATIONS

Prasad et al, "Production of Bioethanol Using Various Agricultural Raw Materials by Two Step Enzymatic Process", Advanced Biotech, pp. 41-43, (Nov. 2009).*
Wu, M.T. et al: "Control of Sucrose Loss in Sugarbeet During Storage by Chemicals1 and Modified Atmosphere and Certain Associated Physiological Changes", Journal of the ASSBT, Jan. 15, 1970, pp. 117-127, XP55004799, Retrieved from the Internet: URL:http://assbt-jsbr.org/JSBR/Vol16/JSBRVol16No2P117to127Controlof SucroseLossinSugarbeetDuringStoragebyChemicalandModifiedA tmosphereandCertainAssociatedPhsiologicalChanges.pdf, [retrieved on Aug. 15, 2011] p. 125-p. 126, p. 118.
Akeson, WR. et al: "Effect of Chemicals on Sucrose Loss in Sugarbeets During Storage", Journal of the ASSBT, Aug. 15, 1978, pp. 255-268, XP55004801, Retrieved from the Internet: URL:http://assbt-jsbr.org/JSBR/Vol20/JSBRVol20No3P255to268EffectofChemicalsonSucroseLossin SugarbeetsDuringStorage.pdf [retrieved on Aug. 15, 2011].

* cited by examiner

*Primary Examiner* — David M Brunsman
(74) *Attorney, Agent, or Firm* — Patent Central LLC; Stephan A. Pendorf

(57) ABSTRACT

The invention relates to the use of an ensiling agent comprising an acidifying formate for the treatment of unchopped beets. In addition, the invention relates to methods for sugar and ethanol production from sugar beets. By using the ensiling agent, sugar degradation can be significantly reduced in sugar beets during storage.

21 Claims, No Drawings

USE OF AN ENSILING AGENT FOR THE TREATMENT OF UNCHOPPED BEETS

This application is a 371 filing of PCT/DE2011/000142, filed Feb. 17, 2011.

The invention relates to the use of an ensiling agent for the treatment of unchopped beets. In addition, the invention relates to a method for sugar and bioethanol production from sugar beets.

Beets in terms of this application include all plants of the species *Beta vulgaris*. These include, for example, beetroot, sugar beet and fodder beet as well as chard.

Sugar beets are used principally for sugar production. For this purpose, they are harvested and processed in special sugar factories. Furthermore, sugar beets have a significant role as a substrate for biogas and bioethanol production.

The particular problem in the utilization of sugar beets, however, is that these beets usually can not be harvested all year round due to local climatic conditions. In many growing areas beets are harvested in the fall of a particular year; however, they cannot all be processed at the same time. Thus, for example, about half of the beets processed in Germany are stored prior to processing. This occurs in part directly on the grounds of the sugar factory; the largest part of the beet harvest is, however, stored locally in piles at the edges of the fields. They are stored aerobically.

This form of storage of harvested sugar beets is problematic, since injured beets in particular loose considerable amounts of their stored sugar (sucrose) during storage. The primary degradation products of sucrose are glucose and fructose, which are subsequently partially further metabolized. This leads to a significant reduction in total sugar content of stored beets, thus commercial viability of white sugar or ethanol production is not achievable following a prolonged storage period. The resulting "processing campaigns" for sugar beets (in Germany about 100 days) very significantly impact the economic competitiveness of white sugar and ethanol production from sugar beets. Attempts have therefore been made to ensile harvested sugar beets, for example in foil tubes.

The ensiling process is divided into different phases: After storage of the plant material and exclusion of air, the residual oxygen contained in the silo is quickly consumed. In the then ensuing anaerobic conditions microorganisms on the substrate surface rapidly grow, especially lactic acid bacteria and yeasts that degrade the available water-soluble carbohydrates (mono- and oligosaccharides) to organic acids and alcohol. Inside the plant material endogenous plant enzymes also degrade carbohydrates to form acids and alcohols. As a result of the lowering of the pH, the growth of undesirable microorganisms and the activity of endogenous plant enzymes are limited, and a stable silage develops.

According to the prior art for ensiling a very fine chopping and high mechanical compaction of the plant material are necessary to
1. minimize air pockets, so that anaerobic conditions can be achieved quickly,
2. better make available carbohydrates for microorganisms by destruction of cellular structures, and
3. promote a rapid diffusion of acids and thus to achieve a pH value reduction throughout the plant material.

Overall, high sugar losses also occur in the ensiling process, especially as the ensiling process takes place not only on the surface of the beet, but the beets "through-ensiles". The sugar will be reduced over the entire cross section of beets.

From DE-OS No. 2,404,462 a method of preserving the sugar content of aerobically stored sugar beets is known, involving use of dilute milk of lime to provide a "disinfectant". For this, burnt lime (CaO) is sprayed onto the sugar beets, or the beets are conveyed through a milk of lime bath. This will give the sugar beet a disinfectant "coating" intended to reduce the sugar-degradation processes which takes place at wound sites under aerobic conditions.

Another method for the preservation of sugar beet is proposed in DD 226 764 A1, wherein silage effluent from silo is used in place of bactericidal or fungicidal chemicals for ensiling. This process involves the storage of freshly chopped beets, preferably in the preservation fluid in non-draining silos without exclusion of air. A complete covering of the beets with preservative fluid is necessary.

Also known is silage of finely chopped sugar beets for animal feed. In order to reduce nutrient loss, DD 59,467 proposes to treat the chopped beets with sodium benzoate as a preservative. In this procedure the fermentation of alcohol and acetic acid is to be reduced, and flow of silage effluent from silo is to be prevented.

Laube et al. (Laube, W;. Weissbach, F;. Budizer, H. H.: Untersuchungen zur Konservierung von Hackfrüchten durch Silierung, Part 1: Die Silierung von Zuckerrüben unter Zusatz verschiedener Konservierungsmittel. In: Archiv für Tierernährung, Volume 18, Issue 3, 1968, pages 229-238. ISSN: 003-942x) also describe the silage of finely shredded sugar beets with sodium benzoate as a preservative. The preservative was mixed into the silage. After a 6-month storage period of the silage, the treated beet pulps were determined to have a higher total sugar content than an untreated control. No details are given however as to the preservation of sucrose or the relative preservation of total sugar.

While an ensiling of chopped or unchopped sugar beets can be advantageous for subsequent biogas production, since ensiled sugar beet matter can be ferment further, the silage is not desirable as a precursor for sugar or ethanol production, since in conventional silage the sugar beet loses considerable amounts of sugar. This loss of sugar is not limited to a sucrose loss. Also, glucose and fructose are lost.

The object of the present invention is therefore to simplify as well as to improve the storage of beet, particularly sugar beet, and thus also to create a possibility of increasing the yield of sugar and bioethanol from stored sugar beets.

According to the invention, the problem is solved by the use of an ensiling agent for the treatment of unchopped sugar beets, in order to reduce the degradation of sugar (sucrose) during storage of the beets. The treatment of unchopped sugar beets with an ensiling agent has, in comparison to the treatment of chopped beets, the further advantage that there is less effluent from silo, which must be dissipated in technically complex manner, and that the treated beets are easily manageable.

It has surprisingly been found that, by external application of an ensiling agent on the unchopped sugar beets, the degradation processes, from rind to the center of the root body, can be significantly reduced. In comparison to untreated controls, in the treated beet, at comparable lowered pH, significantly less sugar is degraded into organic acids and alcohols. Both sucrose and total sugar content remain high after treatment according to the invention. However, the mechanism of signal transduction from the beet surface to the inner regions of the root body is presently not known.

The term "unchopped beets" in the context of this application is understood to include those beets that during harvesting or subsequent handling are separated from certain beet or plant parts. Thus, sugar beets at harvest often have green leafy tops removed or are defoliated. The remaining beet body is considered as an unchopped beet.

As ensiling agents, basically all known ensiling agents can be considered. Suitable ensiling agents, therefore, include biological and chemical ensiling agents. Biological ensiling agents generally include lactic acid producing bacteria. Chemical ensiling agents serve for chemical acidification of the fermentation substrate and thus to suppress fermentation pests. Chemical ensiling agents include organic and inorganic acids or their corresponding salts, and compositions with one or more of these substances.

Preferred ensiling agents therefore are or contain: adipic acid, sodium adipate, potassium adipate; malic acid, potassium malate; ascorbic acid, sodium L-ascorbate, calcium L-ascorbate; succinic acid; acetic acid, potassium acetate, sodium acetate, calcium acetate; fumaric acid; metatartaric acid, calcium tartrate; lactic acid, lactate; phosphoric acid, sodium phosphate, potassium phosphate, calcium phosphate, tartaric acid, sodium tartrate, Rochelle salt (sodium potassium tartrate); tin (II) chloride; citric acid, sodium citrate, potassium citrate, calcium citrate; sulfite; sulfate; nitrite; hexamethylenetetramine; formic acid, formate; propionic acid, propionate; acetic acid, acetate; sorbic acid, sorbate; benzoic acid, benzoate; citric acid; sulfuric acid; hydrochloric acid and nitric acid.

The inventive use relates in particular to the treatment of sugar beets. In general, sugar beets are sown in the spring. They form during the growing season up to the end of September a thick root body that stores the sugar. An uprooting of the sugar beets is then performed from September to mid-November. The harvested sugar beets can then be treated in unchopped form with the ensiling agent and be stored, until its subsequent processing, with exclusion of air, e.g., in foil tubes.

In a particular embodiment of the invention, the ensiling agent comprises a formate, especially tetraformate.

Another, equally preferred embodiment of the invention provides that the ensiling agent comprises a propionate.

Formates are salts of formic acid, propionates are salts of propionic acid. In the case that the ensiling agent is an aqueous solution, the salt contained should be water soluble. Since water-soluble salts of acids dissociate in water and form acid anions, it is also possible to use the respective acids instead of the salts.

The preferred concentration of ammonium tetraformate in the ensiling agent is in the range of 60-90 weight-%, that of ammonium propionate is in the range of 10-30 weight-%.

A particularly suitable ensiling agent (hereinafter "AFP") comprises
60 to 90 weight-% ammonium tetraformate,
10 to 30 weight-% ammonium proprionate,
5-10 wt-% lactic acid,
1-5 wt-% glycerol, and
0.1-0.5 wt-% formamide.

According to a further embodiment of the invention, the ensiling agent is used in liquid form. Here, the ensiling agent is sprayed onto the unchopped beets or the beets are dipped into the ensiling agent. The immersion of the unchopped sugar beets in the liquid ensiling agent has the advantage that the beets completely, that is, from all sides, come into contact with the ensiling agent. After a short exposure time, which only requires for example a few seconds, the treated beets are removed from the liquid ensiling agent. Subsequently, the beets are stored.

The storage of the beets takes place under exclusion of air. For this purpose, the beets are transferred to a container or the like, which is subsequently closed. As a result of the rapid pH drop on the surface and in the interior of the beet, microorganisms on the beet surface and endogenous plant enzymes inside the beet body are largely inactivated. The result is a stable system, in which total sugar and in particular sucrose will be largely preserved.

The storage may be in enclosed facilities, such as in silos or in foil tubes.

The present invention further relates to a method for extracting sugar from sugar beets, comprising the steps of:
a. treatment of unchopped sugar beets with an ensiling agent
b. storage of the unchopped sugar beets under exclusion of air
c. chopping the sugar beets d. extraction of raw juice from the chopped sugar beets
e. extraction of sugar from the raw juice In addition, the invention relates to a method for producing bioethanol from sugar beets. This procedure provides the following steps:
a. treatment of unchopped sugar beets with an ensiling agent
b. storage of the unchopped sugar beets under exclusion of air
c. chopping the sugar beets
d. producing ethanol from the chopped sugar beets The above comments on the composition and the nature of the use of ensiling agent also apply the methods of extracting sugar and producing bioethanol.

After treatment of the unchopped sugar beets they are stored under exclusion of air, as shown above.

With the following examples, the invention is explained in greater detail:

Treatment of Sugar Beets with an Ensiling Agent

Defoliated, washed, unchopped sugar beets (sugar beet storage roots) were immersed for a few seconds in a bath containing the ensiling agent AFP. The application rate was about 2 L/t fresh mass.

The unchopped sugar beets were then transferred into silage casks each with a volume of 120 L and sealed hermetically. The casks were made of plastic and were provided at the bottom with an approximately 15 cm height stainless steel bottom, through which any produced effluent was allowed to run off. Fermentation gas could escape through a mounted fermentation tube. The storage of the casks was carried out at 10° C.

After 90 days, the casks were opened. All of the beets of a barrel were used to prepare a representative beet pulp slurry sample and immediately frozen at −20° C. The results of chemical analysis of the pulp slurry samples are summarized in the following table. The $T_0$ sample is a fraction of the beets used for treatment and silage, taken just prior to the treatment/storage. The controls were beets that had been treated with water instead of the ensiling agent.

|  | pH | Total Sugar (Sucrose, glucose and fructose) in % of fresh mass | Sucrose |
| --- | --- | --- | --- |
| $T_0$ sample | 6.5 | 18.5 | 17.9 |
| Control | 3.5 | 5.6 | 2.5 |
| AFP | 4.0 | 17.8 | 10.7 |

In relation to the respective pre-treatment fresh slurry, about 95% of the total sugar and approximately 60% of sucrose remain preserved in the beets treated with the ensiling agent AFP.

Sugar Production from Sugar Beets after Treatment with an Ensiling Agent

The inventive method for extraction of sugar from unchopped sugar beets takes advantage of the possibility of sugar beet storage, wherein, in comparison to storage without ensiling agent, significantly less sugar is lost. For this purpose harvested sugar beets are treated with ensiling agent as stated above and then stored in silos or in foil tubes. The thus treated and stored sugar beets can then be further processed depending on the available capacity of sugar factories.

In sugar beet factories the sugar beets are cleansed of any debris still present and chopped in a cutting machine. Slender pulps then enter into a scalding tank where they are heated in hot water at c. 70° C. At this temperature, the cell walls of the pulps become permeable, so that the sugar can be extracted from the pulps. This is done in tower systems, where the pulps are de-sugared in countercurrent flow with hot water.

The extracted raw juice contains, in addition to sugar, so-called non-sugar substances, which make the crystallization of sugar more difficult and these are largely removed in the juice purification. To clean, the raw juice is mixed with lime water. The added lime is then precipitated by introducing carbonic acid and the sludge is removed completely after thickening by filtration. As a result of cleansing, the juice produced is a clear, pale yellow thin juice.

The thin juice is concentrated in a multi-stage evaporator to syrup. The further concentration is carried out in steam-heated boiling devices until crystal formation. After boiling, the mixture of sugar crystals and syrup adhering to the crystals is transferred to mashes (tanks with agitators) for cooling and continuation of crystallization. Syrup is separated from sugar crystals in centrifuges. The obtained white sugar is dried, cooled and, after sieving of fine and coarse fractions, is stored in large capacity silos. Raw juice, thin juice and syrup are suitable substrates for ethanol production by microbial fermentation.

The invention claimed is:

1. A method for treating beets to reduce degradation of sugar occurring during storage of the beets, the method comprising:
   treating unchopped beets with an ensiling agent which serves for chemical acidification and
   storing the treated beets under exclusion of air,
   wherein the ensiling agent comprises an acidifying formate, or
   wherein the ensiling agent comprises in addition to ammonium tetraformate and ammonium propionate:
   5-10 wt -% lactic acid,
   1-5 wt -% glycerol and
   0.1-0.5 wt -% formamide.

2. The method according to claim 1, wherein the beet is sugar beet.

3. The method according to claim 1, wherein the formate is tetraformate.

4. The method according to claim 3, wherein the tetraformate is ammonium tetraformate and the concentration of ammonium tetraformate in the ensiling agent is in the range of 60-90 weight -%.

5. The method according to claim 1, wherein the ensiling agent comprises propionate.

6. The method according to claim 5, wherein the propionate is ammonium propionate and the concentration of ammonium propionate in the ensiling agent is in the range of 10-30 weight -%.

7. The method according to claim 1, wherein the ensiling agent is used in liquid form, and wherein the unchopped beets are sprayed with the ensiling agent or dipped into the ensiling agent.

8. The method according to claim 1, wherein the storage of the beets takes place in a hermetically sealed device.

9. The method according to claim 1, wherein the storage of the beets occurs in a foil tube.

10. A method for extraction of sugar from sugar beets, comprising the steps of:
   a. treating unchopped sugar beets with an ensiling agent which serves for chemical acidification,
   b. storing the treated sugar beets under exclusion of air,
   c. chopping the sugar beets,
   d. extracting raw juice from the chopped sugar beets, and
   e. extracting sugar from the raw juice,
      wherein the ensiling agent comprises an acidifying formate, or
      wherein the ensiling agent comprises in addition to ammonium tetraformate and ammonium propionate:
      5-10 wt -% lactic acid,
      1-5 wt -% glycerol and
      0.1-0.5 wt -% formamide.

11. The method according to claim 10, wherein the formate is tetraformate.

12. The method according to claim 11, wherein the tetraformate is ammonium tetraformate and the concentration of ammonium tetraformate in the ensiling agent is in the range of 60-90 weight -%.

13. The method according to claim 10, wherein the ensiling agent comprises a propionate.

14. The method according to claim 13, wherein the propionate is ammonium propionate and the concentration of ammonium propionate in the ensiling agent is in the range of 10-30 weight -%.

15. The method according to claim 10, wherein the ensiling agent is used in liquid form, wherein the unchopped sugar beets are sprayed with the ensiling agent or dipped into the ensiling agent.

16. A method for production of bioethanol from sugar beets, which comprises the following steps:
   a. treating unchopped sugar beets with an ensiling agent which serves for chemical acidification,
   b. storing the treated sugar beets under exclusion of air,
   c. chopping the sugar beets, and
   d. producing ethanol from the chopped sugar beets,
      wherein the ensiling agent comprises an acidifying formate, or
      wherein the ensiling agent comprises in addition to ammonium tetraformate and ammonium propionate:
      5-10 wt -% lactic acid,
      1-5 wt -% glycerol and
      0.1-0.5 wt -% formamide.

17. The method according to claim 16, wherein the formate is tetraformate.

18. The method according to claim 17, wherein the tetraformate is ammonium tetraformate and the concentration of ammonium tetraformate in the ensiling agent is in the range of 60-90 weight -%.

19. The method according to claim 16, wherein the ensiling agent comprises propionate.

20. The method according to claim 19, wherein the propionate is ammonium propionate and the concentration of ammonium propionate in the ensiling agent is in the range of 10-30 weight -%.

21. The method according to claim 16, wherein the ensiling agent is used in liquid form, wherein the unchopped sugar beets are sprayed with the ensiling agent or dipped into the ensiling agent.

* * * * *